United States Patent
Gardiner et al.

(10) Patent No.: US 11,628,092 B2
(45) Date of Patent: Apr. 18, 2023

(54) COMPOSITE FOAM IN WOUND TREATMENT

(71) Applicant: Mölnlycke Health Care AB, Gothenburg (SE)

(72) Inventors: Eric S. Gardiner, Granville, NY (US); Magnus Paledzki, Brunswick, ME (US); Jason Raymond Johnson, Rockland, ME (US)

(73) Assignee: Mölnlycke Health Care AB, Gothenburg (SE)

( * ) Notice: Subject to any disclaimer, the term of this patent is extended or adjusted under 35 U.S.C. 154(b) by 660 days.

(21) Appl. No.: 16/607,439

(22) PCT Filed: May 8, 2018

(86) PCT No.: PCT/EP2018/061872
§ 371 (c)(1),
(2) Date: Oct. 23, 2019

(87) PCT Pub. No.: WO2018/206578
PCT Pub. Date: Nov. 15, 2018

(65) Prior Publication Data
US 2020/0129338 A1  Apr. 30, 2020

(30) Foreign Application Priority Data
May 10, 2017 (EP) ................... 17170446

(51) Int. Cl.
| | |
|---|---|
| *A61F 13/00* | (2006.01) |
| *A61L 15/42* | (2006.01) |
| *C08G 18/10* | (2006.01) |
| *C08G 18/44* | (2006.01) |
| *C08G 18/62* | (2006.01) |
| *C08G 18/73* | (2006.01) |
| *C08G 18/76* | (2006.01) |

(52) U.S. Cl.
CPC .. *A61F 13/00029* (2013.01); *A61F 13/00017* (2013.01); *A61F 13/00042* (2013.01);
(Continued)

(58) Field of Classification Search
CPC ......... A61F 13/00029; A61F 13/00017; A61L 15/425
See application file for complete search history.

(56) References Cited

U.S. PATENT DOCUMENTS 7,759,537 B2    7/2010  Bishop et al.
11,383,484 B2 * 7/2022  Carlsson ................ A61L 15/42
(Continued)

FOREIGN PATENT DOCUMENTS

CN    102112078 A   6/2011
CN    104644339 A   5/2015
(Continued)

OTHER PUBLICATIONS

International Search Report and Written Opinion were mailed on by the International Searching Authority for International Application No. PCT/EP2018/061872, filed on May 8, 2018 and published as WO/2018/206578 on Nov. 15, 2018 (Applicant—Mölnlycke Health Care AB) (15 Pages).

*Primary Examiner* — Michael M Dollinger
(74) *Attorney, Agent, or Firm* — Ballard Spahr LLP (57) ABSTRACT

A composite material is described, which is of particular use in wound treatment, and to a method for producing said composite material is also described. The composite material has a first foam layer having a first hydrophilic polyurethane foam material, and, in immediate contact therewith, a second foam layer having a second hydrophilic polyurethane foam material, which second hydrophilic foam material is different from the first hydrophilic foam material.

16 Claims, 3 Drawing Sheets

(52) U.S. Cl.
CPC ...... *A61F 13/00987* (2013.01); *A61L 15/425* (2013.01); *C08G 18/10* (2013.01); *C08G 18/44* (2013.01); *C08G 18/6225* (2013.01); *C08G 18/73* (2013.01); *C08G 18/7621* (2013.01); *C08G 18/7642* (2013.01); *C08G 2110/0083* (2021.01)

(56) References Cited

U.S. PATENT DOCUMENTS

| | | |
|---|---|---|
| 2003/0149406 A1 | 8/2003 | Martineau et al. |
| 2004/0153040 A1* | 8/2004 | Martineau ............... A61L 15/60 604/304 |
| 2009/0212454 A1 | 8/2009 | Smith et al. |
| 2010/0069858 A1* | 3/2010 | Olson ................. A61F 13/0216 604/319 |
| 2012/0078154 A1* | 3/2012 | Pigg ..................... A61L 15/425 602/46 |
| 2017/0143552 A1* | 5/2017 | Hartwell ........... A61F 13/00068 |
| 2018/0078423 A1* | 3/2018 | Magin ..................... A61L 27/50 |
| 2021/0129483 A1* | 5/2021 | Carlsson ........... A61F 13/00029 |

FOREIGN PATENT DOCUMENTS

| | | | |
|---|---|---|---|
| DE | 102014106518 A1 | 11/2015 | |
| EP | 2659865 A1 | 11/2013 | |
| GB | 2467554 A | 8/2010 | |
| WO | WO 2013/000910 A1 | 1/2013 | |
| WO | WO-2017011050 A2 * | 1/2017 | ....... A61F 13/00017 |
| WO | WO 2017/019868 A1 | 2/2017 | |

\* cited by examiner

COMPOSITE FOAM IN WOUND TREATMENT

CROSS-REFERENCE TO RELATED APPLICATIONS

This application is a U.S. National Phase Application of International Application No. PCT/EP2018/061872, filed May 8, 2018, which claims priority to European Application No. 17170446.3, filed May 10, 2017, each of which are hereby incorporated by reference in their entirety.

FIELD OF THE INVENTION

The present invention relates to a composite foam material, which is of particular use in wound treatment, and to a method for producing the composite material.

BACKGROUND OF THE INVENTION

Wound dressings are used to heal and protect wounds. The capability of the wound dressing to absorb and retain exudate from the wound is of paramount importance for the healing process. The liquid handling capacity of a dressing also affects the frequency of dressing changes, which should be minimized to promote wound healing. In various applications, hydrophilic materials are used in wound dressings to absorb and retain wound fluids, further particularly hydrophilic foams such as hydrophilic open-cell polyurethane foams.

To optimize this liquid handling capacity the wound pad in a wound dressing may preferably include a multiple-layer design, wherein each layer preferably is of a different material, in particular a different foam material, thus having different capabilities and functionalities. To the extent such multiple-layer designs are known from the art, the layers are laminated by means of an adhesive and/or by mechanical lamination. This lamination is associated with several drawbacks. In particular, absorbent materials, for example hydrophilic foams, may swell during use and thus expand when absorbing a liquid, thus stressing the bond between layers and/or increasing thickness, which may result in deformation, e.g. curling or cupping, of dressing and delamination of layers.

U.S. Pat. No. 7,759,537 discloses a multiple-layer wound dressing including inter alia a wound contacting layer and an absorbent core layer, wherein a "keying layer" of a polyamide web, which is a hot melt adhesive, is provided on the absorbent core layer to bind the absorbent core layer to the wound contact layer. Similarly, EP 2 659 865 relates to a multiple-layer wound dressing comprising inter alia a nonwoven layer sandwiched between two foam layers, wherein all layers are bonded together using heat activated bonding webs.

Combining two polyurethane foams to result in a composite material is known, in principle, for example from bicolored foams, or to create a composite material with portions having different physical properties (for example different compression strength). Typically the two foams are prepared separately, using different processing methods.

WO 2013/000910 discloses a composite foam comprising a first foam and a second foam, which foams are at least partially directly connected. The composite foam of WO 2013/000910 is prepared by casting an aqueous emulsion (to obtain the second foam) on a pre-made first foam and cured in place. However, when using the first foam as a casting substrate, it is typically difficult, in practice, to control the final thickness of the second foam. As taught in WO 2013/000910, casting an emulsion containing greater than 40% by weight water onto a foam substrate results in either rapid absorption of water from the emulsion or absorption of the whole emulsion (due to inter alia the force of gravity) into the surface cells of the foam layer substrate. When cured, both phenomena result in a broad (greater than 500 µm) interfacial region that will impede fluid transfer between the foams. In addition, this laminate exhibits severe distortion from puckering that occurs from water absorption into the foam layer substrate.

Hence, there is a need in the art to provide a foam composite material with different areas, in particular layers, of functionalities that keep their functionality during use, in particular during use as a medical dressing, which avoids or minimizes at least one of the disadvantages discussed above, in particular in regard to poor fluid transfer across the interface between two foam layers of different functionalities.

SUMMARY OF THE INVENTION

According to a first aspect of the invention, these and other objects are achieved through a composite material comprising:
  a first foam layer comprising a first hydrophilic polyurethane foam material,
  a second foam layer comprising a second hydrophilic polyurethane foam material,
wherein the fluid retention capacity of said second foam layer is at least 20%, preferably at least 25%, greater than the fluid retention capacity of said first foam layer, wherein said fluid retention capacity is defined as the capability of retaining Solution A having first absorbed a maximum amount of Solution A, according to EN 13726-1:2002, when exposed to a pressure of 40 mmHg for two minutes.

Partly, the present invention is based on the realization that a composite material that comprises at least two different hydrophilic polyurethane foam materials, which are both realized as a layer, and which have different fluid absorbency and/or retention capacity, allows for increased flexibility in regard to the overall fluid management.

In accordance with the present invention, the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

In regard to materials, the term "hydrophilic" generally refers to the water-permeability property of a material or the water-attracting property of a material. In the context of a material with pores (such as, for example, open-cell foams) or materials with through-holes, such a material is typically considered "hydrophilic" if the material takes up water.

In the claims, the terms "comprising" and "comprise(s)" do not exclude other elements or steps, and the indefinite article "a" or "an" does not exclude a plurality of elements or steps. For example, the hydrophilic polyurethane foam material making up a foam layer and comprising a first hydrophilic polymer may comprise additional polymer(s), in particular another polyurethane polymer and/or another (additional) polymer that is not a polyurethane polymer. Also, and further exemplary, more than two layers may be present in the composite material, in particular two or more foam layers.

The mere fact that certain measures are recited in mutually different dependent claims does not indicate that a combination of these measured cannot be used to advantage.

In accordance with the present invention, the term "composite material" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a multicomponent material comprising multiple, different (non-gaseous) phase domains, in which at least one type of phase domain is a continuous phase, preferably in which both phase domains are a continuous phase.

A "layer" as used in accordance with the present invention should be understood to have a continuous extension in one plane (x and y direction) and a thickness perpendicular to said plane (z direction).

In accordance with the invention the "fluid retention capacity" is defined as the capability of retaining Solution A having first absorbed a maximum amount of Solution A, according to EN 13726-1:2002, when exposed to a pressure of 40 mmHg for two minutes. The fluid retention capacity is herein expressed in the unit of mass (kg) of retained Solution A per volume ($m^3$) of foam material.

Solution A, as defined in EN 13726-1, consists of a sodium chloride and calcium chloride solution containing 142 mmol of sodium ions and 2.5 mmol of calcium ions as the chloride salts. This solution has an ionic composition comparable to human serum or wound exudate. Said solution is prepared by dissolving 8.298 g of sodium chloride and 0.368 g of calcium chloride dihydrate in deionized water up to the "1 L" marking in a volumetric flask.

In embodiments of the invention, the thickness of the first foam layer is less than the thickness of the second foam layer, preferably wherein the thickness of the first layer is less than 40% of the total thickness of the composite material. Thereby, a rapid transport through the first foam layer to the second foam layer is facilitated.

Preferably, the composite material may be comprised in a medical dressing (e.g. wound dressing), and the first foam layer may be adapted to function as the wound contact layer and/or the wound fluid acquisition layer, wherein the second foam layer may be adapted to function as the wound fluid retention layer. In such dressing configuration, it is advantageous that fluid is rapidly absorbed into the first foam layer and subsequently transported into the second foam layer. By adapting the thickness of the first foam layer, such that it is less than the thickness of the second layer, the transportation of wound fluids through the first foam layer to the second foam layer may be optimized.

In embodiments of the invention, the first foam layer has a thickness of from 0.5 mm to 2.5 mm, preferably from 1.0 mm to 2.0 mm, such as 1.5 mm.

In embodiments of the invention, the second foam layer has a thickness of from 1.5 to 7.0 mm, preferably from 2.0 mm to 5.0 mm, such as 3.5 mm.

In embodiments of the invention, the combined thickness of the first foam layer and the second foam layer is from 3 to 8 mm, preferably from 3 to 6 mm, such as 5 mm.

In embodiments of the invention, the first foam layer is characterized by a free swell absorptive capacity, corresponding to the maximum absorptive capacity, of from 500 to 1200 $kg/m^3$, preferably from 600 to 1000 $kg/m^3$, as measured by EN 13726-1:2002.

In embodiments of the invention, the second foam layer is characterized by a free swell absorptive capacity, corresponding to the maximum absorptive capacity, of from 800 to 2500 $kg/m^3$ as measured by EN 13726-1:2002.

In embodiments of the invention, the second foam layer has a fluid retention capacity of at least 800 $kg/m^3$, preferably at least 900 $kg/m^3$, more preferably at least 1000 $kg/m^3$.

In embodiments of the invention, the second foam layer has a fluid retention capacity corresponding to at least 80%, preferably at least 85%, of its free swell absorptive capacity.

In embodiments of the invention, the fluid retention capacity of the second foam layer is at least 30%, preferably at least 40%, greater than to the fluid retention capacity of the first foam layer. In embodiments of the invention, the fluid retention capacity of the second foam layer is at least 50%, preferably at least 100%, more preferably at least 150% greater than the fluid retention capacity of the first foam layer.

In embodiments of the invention, the first foam layer has a fluid retention capacity corresponding to less than 80% of its free swell absorptive capacity In embodiments of the invention, the first foam layer has a speed of absorption of at least 10 μL/sec, preferably at least 20 or at least 30 μL/sec. For example, the first foam layer has a speed of absorption of 10 to 40 μL/sec.

In embodiments of the invention, the second foam layer has a speed of absorption of at least 1 μL/sec, preferably at least 3 μL/sec, or at least 5 μL/sec. For example, the second foam layer has a speed of absorption of 1 to 20 μL/sec, such as 2 to 15 μL/sec.

In accordance with the invention, the term "speed of absorption" is defined as the speed of absorbing a given volume of a fluid (volume/time) as measured according to TAPPI standard T558 OM-97 using 30 μL of Solution A according to EN 13726-1:2002, as test solution.

In embodiments of the invention, the first foam layer has a speed of absorption that is at least 100%, preferably at least 200%, further preferably at least 300%, higher than the speed of absorption of the second foam layer. For example, in embodiments of the invention, the speed of absorption is at least 400%, preferably at least 500% or 600%, higher than the speed of absorption of the second foam layer.

In embodiments of the invention, at least one of the first and second foam layer comprising the first and second hydrophilic polyurethane foam material, respectively, is obtained or has been obtained by a process, in which an aqueous mixture comprising a prepolymer, leading to the hydrophilic polyurethane foam layer, comprises less than 40% of water, preferably less than 30% of water.

For example, in embodiments of the invention, the water content of said aqueous mixture is 10 to 30% w/w, such as 10 to 25% w/w In embodiments of the invention, the first and the second hydrophilic polyurethane foam material are selected from an open-cell porous hydrophilic foam having a density of 60 to 180 $kg/m^3$ as measured according to standard method ISO 845:2006.

As used herein, the term "open-cell" refers to the pore structure of the foam, wherein the pores in a pore structure are connected to each other and form an interconnected network with pathways for fluid flow through the foam material.

In embodiments of the invention, the first hydrophilic polyurethane foam material and the second hydrophilic polyurethane foam material have a porosity of at least 70%, preferably at least 80%, wherein the pores represent an essentially open-cell pore structure.

The composite according to the present invention may particularly advantageously be used in wound treatment to absorb and retain fluid (e.g. wound exudate) from a wound site. The first foam layer comprising a first hydrophilic polyurethane foam material, which is typically arranged to be in contact with a wound site, may advantageously be adapted to have absorption properties that support comparatively rapid absorption, or wicking, of wound exudate into the composite material, wherein the second foam layer comprising the second hydrophilic polyurethane foam material (and typically arranged to be farther away from the wound) may advantageously be adapted to have comparatively high fluid (e.g. wound exudate) retention capacity such that wound exudate is retained therein.

In accordance with the present invention, the term "wound site" or "wound" is to be understood as any open or closed wound, for example, including inter alia (but not limited to) chronic wounds, acute wounds, and post-operative wounds such as e.g. closed incisions and scar treatment.

Accordingly, in one embodiment, when the composite material is used in wound treatment, the first foam layer may advantageously be adapted be in contact with the wound site to facilitate such absorption and/or transfer of wound exudate from the wound site to the second foam layer.

In accordance with a second aspect of the present invention, the composite material comprises:

a first foam layer comprising a first hydrophilic polyurethane foam material, wherein the first foam layer has a first side adapted to face an area of application in use, preferably adapted to face a wound area; and a second foam layer comprising a second hydrophilic polyurethane foam material, wherein a plurality of channels extends from the first side of the first foam layer through the entire first foam layer into at least a portion of the second foam layer, wherein the channels have an average diameter of from 0.1 mm to 4.0 mm, preferably from 0.5 mm to 3.0 mm, further preferably from 1.5 mm to 2.5 mm The plurality of channels provided in the first foam layer, and extending into at least a portion of the second foam layer, facilitates both initial absorption of fluids, such as e.g. wound exudates, as well as the transport of fluids through the first foam layer and across the interface between the first foam layer and the second foam layer, such that the overall transport of fluid from the first side of the foam layer into the second foam layer is improved.

In embodiments of the invention, the first side of the first foam layer is at least partly coated with an adhesive, such as for example, a silicone based adhesive, wherein a plurality of channels extends through the entire first foam layer, and further extends into at least a portion of the second foam layer. The adhesive coating, which may function to adhere the first side of the first foam layer to a wound site, may occlude at least some of the open foam pores present at the first side of the first foam layer, which may reduce the absorption capacity of fluid in the first foam layer. However, by providing the plurality of channels in the first foam layer, the absorption capacity can be remain or even improved even in the presence of an adhesive coating. The plurality of channels may be provided before or after the first side is coated with the adhesive, preferably before the first side is coated with the adhesive. The plurality of channels may be particularly useful to improve absorption of thick wound exudate.

In accordance with the second aspect, the term "channel" is to be understood as referring to generally open structures, i.e. structures that allow for the through-flow of fluids (liquids or gases) and, unless filled with a fluid during the intended use, are not obstructed by the material making up the layer, in particular the hydrophilic polyurethane foam material. In embodiments, these channels are "open" in the above-described sense over essentially their entire length.

In particular, while these channels may be filled with fluid during intended use, these channels retain an open structure in the sense that the channels are not permanently closed to liquid flow during use, including during use in the presence of materials that may increase in density during use, for example due to swelling.

It is understood that the (average) diameter of these channels may increase or (more typically) decrease during use, but not to an extent that essentially all channels are closed to essentially all fluid flow. In embodiments of the invention, the channels are characterized by an aspect ratio, i.e. ratio of (average) open length to (average) open diameter of at least 1:1, preferably at least 2:1, further preferably at least 5:1.

In embodiments of the invention, said channels are arranged essentially perpendicular to the first foam layer and the second foam layer, and therefore also essentially perpendicular to the interface between those two layers.

In embodiments of the invention, no channels are present in at least 20%, preferably in at least 30%, of the overall area of the first side of the first foam layer. For example, in embodiments of the invention, the overall area of the first side of the first foam layer comprises a first central portion and second portion surrounding the first portion, wherein channels are only present in the first central portion, and wherein the area of the second portion is at least 20% of the overall area of the first side of the first foam layer.

In embodiments of the invention, the channels are arranged in patterns.

In embodiments of the invention, the channels form a continuous pattern of square(s) on the area of the first side of the first foam layer, or of circle(s) growing out from the center of the area of the first side of the first foam layer, In embodiments of the invention, the channels form ornamental or informative patterns, such as waves or text communicating a message.

In embodiments of the invention, at least a part of the plurality of channels has a diameter that varies along its length and/or at least one subset of channels has a diameter that is different from the diameter of another subset of channels.

In embodiments of the invention, the area density of channels per overall area of the first side of the first foam layer, is from 0.5 channel per square centimeter to 200 channels per square centimeter, preferably from 1 channel per square centimeter to 100 channels per square centimeter, more preferably 1 channel per square centimeter to 50 channels per square centimeter.

The above-described embodiments of channels, alone or in combination, allow for adjusting the fluid directing properties to the specific situation at hand, for example specific fluid viscosity, specific flow rate, specific intended use etc.

In embodiments of the invention, the plurality of channels are formed by way of punching (e.g. using a rotating die cut, or needles), heated pins, and/or laser beam application, for example.

The embodiments, features and effects described in connection with the composite material according to the first (above) and third (below) aspects of the invention are applicable, mutatis mutandis, for the above described composite material according to the second aspect of the invention.

According to a third aspect of the invention, the objects discussed above and other object are achieved through a composite material comprising:
- a first foam layer comprising a first hydrophilic polyurethane foam material,
- a second foam layer comprising a second hydrophilic polyurethane foam material,
- wherein an interfacial bonding volume exists between said first and said second foam layer,
- wherein said interfacial bonding volume comprises a mixture of the materials making up said first and said second foam layer,
- and wherein said interfacial bonding volume has a thickness of less than 200 μm, preferably less than 100 μm, further preferably 50 μm or less.

In accordance with these embodiments, a composite material is provided that comprises a first foam layer which is directly bonded to (e.g. by physical "adhesive" interaction), and thus in immediate contact with, a second foam layer.

In accordance with these embodiments, the need of providing "extraneous" bonding means to hold the first and the second layer together, e.g. by means of providing an adhesive layer between the foam layers, is obviated. Dispensing with a (separate) adhesive layer is advantageous with regard to, inter alia, fluid transport between the foam layers, since the presence of additional bonding means, such as an adhesive layer, may reduce or inhibit fluid transfer between bonded layers.

In embodiments of the invention, at least one physical property of the material comprised in the interfacial bonding volume is different vis-à-vis the material making up the first foam layer and the second foam layer, respectively. For example, the material within the interfacial bonding volume may have a higher density or different foam structure, e.g. different pore size, vis-à-vis first foam layer and the second foam layer, respectively.

In embodiments of the invention, the "thickness", i.e. the extension of the interfacial bonding volume perpendicular to the xy-plane as defined by the first and the second foam layer, of the interfacial bonding volume between the first and the second foam layers is in the range of 25 to 200 μm, preferably 25 to 100 μm.

Minimizing the interfacial bonding volume is advantageous as the absorption and/or retaining capacity of the materials may be reduced in the interfacial bonding volume. Thus by minimizing the interfacial bonding volume (i.e. the thickness thereof) the transfer of fluid between layers is expected to be facilitated and improved.

The term "interfacial bonding volume" as used in accordance with the present invention is understood to relate to a volume at the interfacial region between the first foam layer and the second foam layer, which volume comprises both (e.g. a mixture thereof) the first hydrophilic polyurethane foam material and the second hydrophilic polyurethane foam material, which materials are bonded together in said interfacial volume. The thickness of the interfacial volume refers to the thickness (or interfacial penetration depth) in the direction of the thickness of the foam layers.

The interfacial bonding volume is a distinct phase within the overall composite material that can be distinguished from the "pure" first and second foam layer, respectively, for example by optical microscopy. The different phases (interfacial bonding volume, "pure" first and second foam layers) can also be distinguished based on differences in physical properties, for example based on differences in density and/or differences in pore size and distribution.

In embodiments of the invention, the fluid retention capacity of the second foam layer is at least 20%, preferably at least 25%, greater than the fluid retention capacity of said first foam layer, wherein said fluid retention capacity is defined as the capability of retaining Solution A having first absorbed a maximum amount of Solution A, according to EN 13726-1:2002, when exposed to a pressure of 40 mmHg for two minutes.

In embodiments of the invention, the second foam layer has a fluid retention capacity of at least 800 kg/m$^3$, preferably at least 900 kg/m$^3$.

The embodiments, features and effects described above in connection with the composite material according to the first and second aspects of the invention are applicable, mutatis mutandis, for the above described composite material according to the third aspect of the invention.

According to a fourth aspect of the invention, the above-discussed and other objects are achieved through a method of making a composite material, said method comprising the steps of:
- (i) preparing an aqueous mixture comprising a polyurethane prepolymer, wherein the water content of said aqueous mixture is less than 40% w/w, preferably less than 30% w/w, preferably less than 25% w/w, relative to the total weight of said aqueous mixture;
- (ii) applying said aqueous mixture from step (i) onto a carrier material;
- (iii) applying, before said aqueous mixture is essentially completely cured, an already cured hydrophilic polyurethane foam layer on top of said aqueous mixture as cast onto said carrier material in step (ii);
- (iv) allowing said aqueous mixture to essentially completely cure, thereby producing a composite material comprising a first foam layer comprising a first hydrophilic polyurethane foam material and a second foam layer comprising a second hydrophilic polyurethane foam material.

In embodiments of the invention, the above described method further advantageously comprises a step (v) of drying the composite material.

The term "cure" as used in accordance with the present invention means formation of (cross-linking) bonds between the polymers of the prepolymer in the aqueous mixture, in particular the (cross-linking) bond is or comprises urethane bond formed through reaction between an hydroxyl group on a first polymer and an isocyanate (NCO) group on a second polymer, or a urea bond formed through reaction between an amine group on a first polymer and an isocyanate (NCO) group on a second polymer.

In embodiments of the invention, the degree of curing of the aqueous mixture is between 50 to 90%, preferably 70 to 90%, at the stage of applying said layer of an already cured hydrophilic polyurethane foam layer in step (iii). By adapting the degree of curing of the aqueous mixture, sufficient binding between the first and second foam layers can be achieved whilst concurrently and advantageously minimizing the interfacial bonding volume (i.e. the thickness thereof). The peel strength between the first foam layer and the second foam layer can thus be adapted such that it exceeds the (tensile) strength of the weakest foam layer, and a peel strength testing would lead to failure in one of the layers and not within the interfacial bonding volume.

Steps (i)-(iii) are advantageously performed as immediately successive steps to ensure a desirable degree of curing in the aqueous mixture when the already cured foam layer is applied, thereby ensuring sufficient bonding between the foam layers (in the interfacial bonding volume thus created).

The term "degree of curing" as used herein relates to the percentage of isocyanate groups that have reacted, as measured by Fourier Transform Infrared Spectroscopy (FTIR). In this context, a 100% degree of curing means that essentially all isocyanate (NCO) groups have reacted, whereas 0% degree of curing means that essentially no isocyanate (NCO) groups have reacted. The amount of NCO groups, and thus the corresponding degree of curing, at different stages of the method of producing the composite material can be monitored by FTIR. The number NCO groups corresponding to 0% degree of curing is measured before the prepolymer composition is mixed with water, i.e. before step step (i). The terms "completely cured" and "cure completely" as used in accordance with the present invention mean a degree of curing of 90-100%.

The inventors have surprisingly realized that a (already cured) foam layer comprising a hydrophilic foam material can advantageously be directly attached to another foam layer comprising a hydrophilic foam material, by applying the (already cured) foam layer on top of a curing aqueous prepolymer mixture of the other foam layer. Without wishing to be bound by theory, it is believed that the comparatively low water content in the aqueous prepolymer mixture, in accordance with the present invention, avoids or minimizes the rapid absorption of aqueous prepolymer mixture into the other (already cured) foam, which absorption would otherwise create an undesirable large interfacial bonding volume (i.e. large thickness thereof) between layers and/or result in a composite material wherein the two foam materials are completely integrated.

In embodiments of the invention, the step (i) of preparing an aqueous mixture comprising a prepolymer includes the step of mixing said prepolymer with water.

In embodiments of the invention, the water content of said aqueous mixture is less than 30% w/w (relative to the total weight of the aqueous mixture), preferably less than 25% w/w. In embodiments of the invention, the water content of said aqueous mixture is 5 to 40% w/w. In embodiments of the invention, the water content of said aqueous mixture is 5 to 30% w/w. In embodiments of the invention, the water content of said aqueous mixture is from 5 to 25% w/w. In embodiments of the invention, the water content of said aqueous mixture is 5 to 20% w/w. In embodiments of the invention, the water content of said aqueous mixture is 10 to 40% w/w. In embodiments of the invention, the water content of said aqueous mixture is 10 to 30% w/w. In embodiments of the invention, the water content of said aqueous mixture is from 10 to 25% w/w. In embodiments of the invention, the water content of said aqueous mixture is 15 to 20% w/w.

The water content in the aqueous mixture may advantageously be adapted such that the minimum amount of water required to produce a foam is used. Minimizing the use of water in the aqueous mixture is advantageous inter alia in the drying step (v) of the method as low amount of water in the composite material means a low shrinkage of the layers in the composite during the drying step, which thus reduces the stress on bonds between the layers. Minimizing the amount of water in the aqueous mixture provides for an aqueous mixture with a higher viscosity which is advantageous in order to minimize penetration of the aqueous mixture into the foam layer of the already cured foam.

In embodiments, the thickness of the aqueous mixture as applied in step (ii) is from 0.5 mm to 5 mm.

In embodiments of the invention, the aqueous mixture further comprises at least one surfactant, preferably a non-ionic surfactant.

In embodiments of the invention, the applying (casting) step (ii) is preferably performed by the "coat hanger die" method, to leave the top surface of the aqueous mixture free for bonding of the second foam layer.

The already (completely) cured hydrophilic polyurethane foam is bonded on top of the aqueous mixture in application step (iii). "Applying" step (iii) can be implemented by all methods known to the skilled person, e.g. casting to thickness between carriers or cast thick and skived to dimension.

In embodiments of the invention, the already cured hydrophilic foam is the first foam layer according to the invention, wherein the second foam layer is produced from said aqueous mixture. Accordingly, the foam layer with less retention capacity, that is the first foam layer according to the first aspect of the invention, is applied to the curing aqueous mixture of the second foam layer (in step (iii)). Implementing this specific sequence is advantageous as absorption of the aqueous mixture into the first foam layer, and, associated therewith, increase of the thickness of the interfacial volume, can be minimized, as opposed to applying a pre-made second foam layer with high retention capacity on top of a curing aqueous mixture of the first foam layer having less retention capacity.

In embodiments of the invention, the above described method may further include a step of providing a plurality of channels, extending from the first side of the first foam layer, across the interface between the first foam layer and the second foam layer, and into at least a portion of the second foam layer. The plurality of channels may be formed by way of punching (e.g. using a rotating dye cut, or needles), heated pins, and/or laser beam application, for example.

Features and effects of this fourth aspect of the present invention are largely analogous to those described above in connection with the first, second and third aspects of the present invention. Embodiments disclosed herein in regard to the first, second and third aspects apply to the fourth aspect mutatis mutandis.

According to a fifth aspect of the invention, the above-mentioned and other objects are achieved by means of providing a medical dressing (in particular a wound dressing) comprising the composite material according to the invention.

In embodiments of the invention, the medical dressing further comprises at least one further layer, preferably a backing and/or an adhesive layer or coating, preferably two or more of these further layers.

The person skilled in the art realizes that the present invention by no means is limited to the exemplary embodiments described herein. For example, the medical dressing according to invention may comprise additional structural layer(s) in fluid communication with the composite material to further optimize desirable properties and/or to achieve additional functionalities.

In embodiments of the invention, the first hydrophilic polyurethane foam material, as used in all embodiments of the present invention described above, is obtained from a first prepolymer comprising or being an isocyanate-capped polyol or isocyanate-capped polyurethane, and/or wherein the second hydrophilic polyurethane foam material, as used in all embodiments of the present invention described above, is obtained from a second prepolymer comprising or being an isocyanate-capped polyol or isocyanate-capped polyurethane. In embodiments of the invention, the first prepolymer and the second prepolymer are different.

In accordance with the present invention, the term "prepolymer" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a polymer or oligomer the molecules of which are capable of entering, through reactive groups, into further polymerization and thereby contributing more than one structural unit to at least one type of chain of the final polymer.

In embodiments of the invention, the first and/or the second prepolymer derive(s) from a reaction between a polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the polyol is selected from the group consisting of polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols, among others, in particular polycondensates of di or optionally tri-, and tetraols as well as di or optionally tri- and tetracarboxylic acids or hydroxycarboxylic acids or lactones.

Exemplary suitable diols are ethylene glycol, butylene glycol, diethylene glycol, triethylene glycol, polyalkylene glycols such as polyethylene glycol, and also 1,2-propanediol, 1,3-propanediol, 1,3-butanediol, 1,4-butanediol, 1,6-hexanediol and isomers, neopentyl glycol or neopentyl glycol hydroxypivalate, In addition, polyols such as trimethylolpropane, glycerol, erythritol, pentaerythritol, trimethylolbenzene or trishydroxyethyl isocyanurate are also within the scope of the present invention.

In embodiments of the invention, the first and/or the second prepolymer derives from a reaction between a polyol and a diisocyanate compound that is aliphatic. For example, in embodiments of the invention, the diisocyanate compound is or comprises hexamethylene diisocyanate (HDI). Accordingly, in embodiments of the invention, the first and/or the prepolymer is or comprises an hexamethylene isocyanate-capped polyol or hexamethylene isocyanate-capped polyurethane.

In embodiments of the invention, the first and/or the second prepolymer is or comprises a hexamethylene isocyanate-capped polyethylene glycol.

In embodiments of the invention, the first and/or the second prepolymer derives from a reaction between said polyol and a diisocyanate compound that is aromatic. For example, in embodiments of the invention, the diisocyanate compound is or comprises toluene diisocyanate (TDI), methylene diphenyl diisocyanate (MDI). Accordingly, in embodiments of the invention, the first and/or the second prepolymer is or comprises a toluene isocyanate-capped polyol or a methylene diphenyl isocyanate-capped polyol or toluene isocyanate-capped polyurethane or methylene diphenyl isocyanate-capped polyurethane.

In embodiments of the invention, the first and/or the second prepolymer is or comprises a toluene isocyanate-capped polyethylene glycol. In embodiments of the invention, the first and/or the second prepolymer is or comprises a methylene diphenyl isocyanate-capped polyethylene glycol.

In embodiments of the invention, the first hydrophilic foam material is obtained from a first prepolymer that derives from a reaction between a first polyol and a first diisocyanate compound, wherein the second hydrophilic foam material is obtained from a second prepolymer that derives from a reaction between a second polyol and a second diisocyanate compound. In embodiments of the invention, the first and the second diisocyanate compounds are same, such as one of hexamethylene diisocyanate (HDI), toluene diisocyanate (TDI), methylene diphenyl diisocyanate (MDI), or isophorone diisocyanate (IPDI). In embodiments of the invention, the first and the second diisocyanate compounds are different, for example the first diisocyante compound may be toluene diisocyanate (TDI), wherein the second diisocyanate compound may be hexamethylene diisocyanate (HDI). In embodiments of the invention, the first and second polyol may be same, for example, the first and second polyol may be polyethylene glycol (polyethylene oxide). In embodiments of the invention, the first and the second polyol are different. In embodiments of the invention wherein the first prepolymer and the second prepolymer are different, the first prepolymer may be a toluene isocyanate-capped polyethylene glycol, wherein the second prepolymer may be hexamethylene isocyanate-capped polyethylene glycol or a methylene diphenyl isocyanate-capped polyethylene glycol.

In embodiments of the invention, the first and/or the second foam layer comprise(s) an antimicrobial agent. In embodiments of the invention, the antimicrobial agent comprises silver. In embodiments of the invention, the silver is metallic silver. In embodiments of the invention, the silver is a silver salt. In embodiments of the invention, the silver salt is silver sulfate, silver chloride, silver nitrate, silver sulfadiazine, silver carbonate, silver phosphate, silver lactate, silver bromide, silver acetate, silver citrate, silver CMC, silver oxide. In embodiments of the invention, the silver salt is silver sulfate. In embodiments of the invention, the antimicrobial agent comprises a monoguanide or biguanide. In embodiments of the invention, the monoguanide or biguanide is chlorhexidine digluconate, chlorhexidine diacetate, chlorhexidine dihydrochloride, polyhexamethylene biguanide (PHMB) or a salt thereof, or polyhexamethylene monoguanide (PHMG) or a salt thereof. In embodiments of the invention, the biguanide is PHMB or a salt thereof. In embodiments of the invention, the antimicrobial agent comprises a quaternary ammonium compound. In embodiments of the invention, the quaternary ammonium compound is cetylpyridinium chloride, benzethonium chloride, or poly-DADMAC. In embodiments of the invention, the antimicrobial agent comprises triclosan, sodium hypochlorite, copper, hydrogen peroxide, xylitol, or honey.

BRIEF DESCRIPTION OF THE DRAWINGS

These and other aspects of the invention will now be shown in more detail, with reference to the Figures showing an exemplary embodiment of the invention, wherein.

DESCRIPTION OF EMBODIMENTS OF THE INVENTION

In the following, detailed embodiments of the present invention are described, with reference to the accompanying Figures, which are exemplary illustrations of embodiments of the invention.

Figure 1:
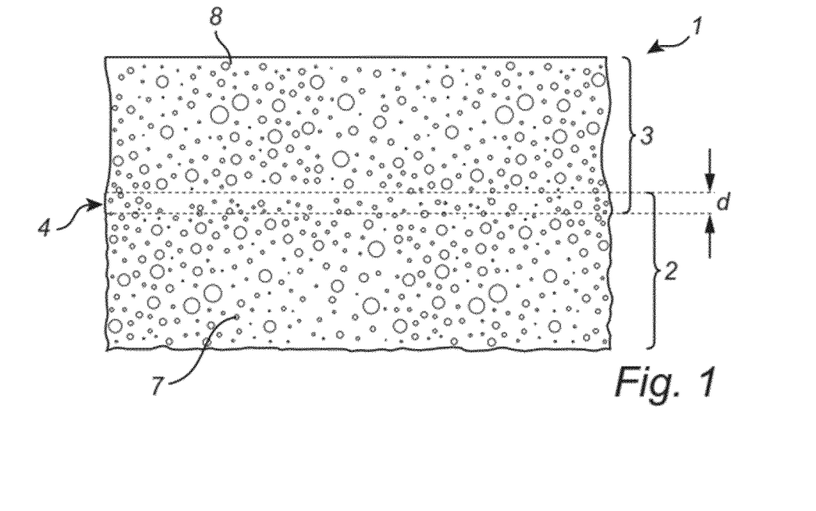
FIG. 1 is a cross-sectional view of an embodiment of a composite material according to the invention.

FIG. 1 illustrates an embodiment of a composite material 1 according to the invention. The composite material 1 comprises a first foam layer 2 comprising a first hydrophilic foam material of a hydrophilic polyurethane foam material 7; and a second foam layer 3 comprising a second hydrophilic foam material 8.

As illustrated in FIG. 1, an interfacial bonding volume 4 exists between the first foam layer 2 and the second foam layer 3, wherein—as generally applicable to all embodiments disclosed herein—the interfacial bonding volume 4 comprises no material other than the materials making up the first 2 and the second 3 foam layer, respectively.

The first foam 2 and the second foam layer 3 are directly bonded to each other, at the interfacial bonding volume 4, by means of, e.g., physical interactions, thereby avoiding the need of additional bonding means, such as, for example, an additional adhesive layer between the foam layers 2, 3. This is advantageous as such an additional adhesive layer may reduce the moisture vapor transmission rate (MVTR) through the composite material 1 and, in fact, trap the fluid (e.g. wound exudate if composite material is used as, or in, a medical dressing) in one of the foam layers. For example, if the composite material 1 is used as or in a medical dressing, wherein the first foam layer 2 is adapted to be in contact with, and/or to face, a wound, any exudate absorbed by the first foam layer 2 can be transferred to the second foam layer 3 without having to pass through an additional adhesive layer.

In embodiments of the invention, the thickness d of the interfacial bonding volume 4 is less than 200 μm, preferably less than 100 μm, more preferably less than 50 μm. For example, in embodiments of the invention the thickness d of the interfacial bonding volume 4 is in the range of 10 to 200 μm, such as 50 to 200 μm or 50 to 150 μm, or 50 to 100 μm. In embodiments of the invention, the thickness d of the interfacial bonding volume 4 is in the range of 10 to 100 μm, such as 10 to 60 μm. A minimum thickness d of the interfacial bonding volume 4 is advantageous as the absorption and/or retaining capacity of the materials may be impaired in the interfacial bonding volume 4, and a small thickness d of the interfacial bonding volume 4 facilitates fluid transfer between the foam layers 2, 3.

The composite foam material 1 in accordance with embodiments of the present invention allows to (more) strongly bond together two hydrophilic foam layers. Since no adhesive or other material that would be different from the material(s) making up the two layers is present at the interface between the two layers, fluid transfer from one layer to the other is optimized. Together with the possibility to adjust different functionalities in the two layers, this allows, in particular, to optimize absorption and retention in one overall foam material. This also allows for providing a multilayer, in particular bilayer, foam composite, which has an active ingredient, for example an antimicrobial agent, in only one layer, thus saving costs.

For example, in embodiments of the present invention a composite foam 1 is provided, in which the wound contact layer (e.g. the first foam layer 2) can be optimized for quick absorption and subsequent layers (e.g. the second foam layer 3) can be optimized to have a high fluid retention capacity. Similarly, the present invention allows to incorporate an active substance (such as an anti-microbial compound) in the wound contact layer while still retaining a foam with good absorption and good overall foam retention otherwise.

FIGS. 2*a-e* illustrate exemplary embodiments of medical dressings 40, 50, 60, 80, 90 comprising the composite material 1, as realized in the form of a sequence of layers, according to the invention. The medical dressings 40, 50, 60, 80, 90 shown in FIGS. 2*a-e* thus comprise the first foam layer 2 comprising the first hydrophilic polyurethane foam material 7 and the second foam layer 3 comprising the second hydrophilic polyurethane foam material 8.

In embodiments of the invention, as shown in FIGS. 2*a-e*, the medical dressings 40, 50, 60, 80, 90 further comprise a backing layer 21, 23 overlaying a top side 31 of the second foam layer 3, wherein the top side 31 being opposite to the side bonded to the first foam layer 2. Thereby, the first foam layer 2 has a wound facing side 35 which can function as a direct or indirect wound contact layer, to absorb and retain wound exudate and/or transport wound exudate from the wound to the above second foam layer 3. In this configuration, wherein the first foam layer 2 is facing the wound, the first foam layer 2 can advantageously be adapted to provide rapid absorption of wound exudate. For example, in embodiments of the invention, the first foam layer 2 has a speed of absorption of at least 10 μL/sec, preferably at least 30 μL/sec.

Figure 2A:
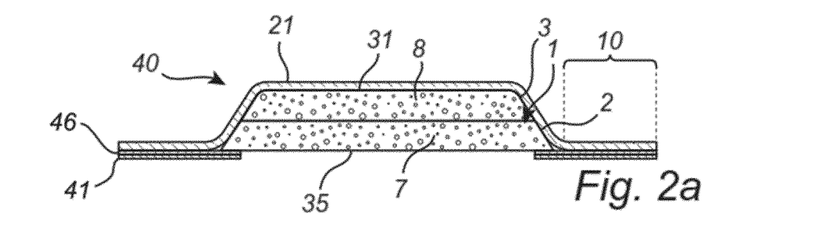
FIGS. 2a-e are cross-sectional views of embodiments of a medical dressing according to the fifth aspect of the invention.
Figure 2B:
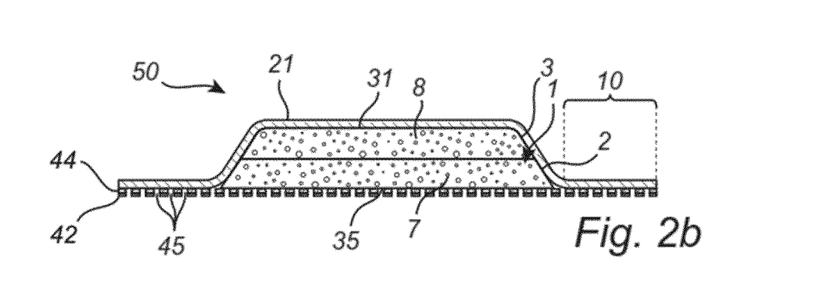

In embodiments of the invention, as shown in FIGS. 2*a-b*, the backing layer 21 extends outside the peripheral portion of the layers of the composite material 1, to define a border portion 10 of the backing layer thus surrounding the peripheral portion of the layers of the composite material, thereby providing a so-called island dressing.

Suitable backing layers 21, 23 are, for example, films, foils, foams, or membranes. Furthermore, it is advantageous if the backing layer has a thickness in the area of from ≥5 μm up to ≤80 μm, particularly preferred of from ≥5 μm up to ≤60 μm, and particularly preferred of from ≥10 μm up to ≤30 μm and/or that the backing layer has an elongation at break of more than 450%.

The backing layer 21, 23 may be realized to be pervious to water vapor in accordance to DIN 53333 or DIN 54101.

Preferably, the backing layer 21, 23 may comprise a thermoplastic polymer, for example as a coating, or may consist thereof. A thermoplastic polymer, at first, is to be understood as a polymer that remains thermoplastic if the same is repeatedly heated and cooled within a temperature that is typical for the respective processing or application conditions. Being thermoplastic is understood to be the property of a polymer material to repeatedly soften upon application of heat and to repeatedly harden when cooled down, within a temperature range that is typical for the respective material, wherein the material remains capable of being formed, in the softened stage, and repeatedly, by way of flowing, for example as a shaped article, extruded or otherwise.

Preferred thermoplastic polymers are polyurethane, polyethylene, polypropylene, polyvinyl chloride, polystyrene, polyether, polyester, polyamide, polycarbonate, polyether polyamide copolymers, polyacrylate, polymethacrylate, and/or polymaleate. Preferably, the thermoplastic polymers are elastomeric. It is particularly preferred that the carrier foil comprises thermoplastic polyurethanes (TPU), or consists thereof. Thermoplastic polyurethanes selected from the group comprising aliphatic polyester polyurethanes, aromatic polyester polyurethanes, aliphatic polyether polyurethanes and/or aromatic polyether polyurethanes are particularly suitable. By using these polymers, it is possible to obtain backing layers as breathable elastic membrane films. These are characterized by high flexibility and elasticity over a broad range of temperatures, also having advantageous sealing properties for (liquid) water while having a high water vapor permeability. These materials are further characterized by low noise, advantageous textile feel, resistance against washing and cleaning, very good chemical and mechanical resistance and the fact they are free of plasticizers.

Particularly preferred is also a backing layer that acts as a barrier for germs and has a high sealing capability against exudate emanating from the wound while, at the same time, being permeable for water vapor. In order to achieve the same, the backing layer may, for example, be realized as a semipermeable membrane.

In embodiments of the invention, the backing layer 21, 23 is preferably vapor permeable. The backing layer 21, 23 may be a plastic film, for example, comprising or consisting of polyurethane, polyethylene, or polypropylene. In embodiments of the invention, the backing layer 21, 23 is a polyurethane film having a thickness in the range of 10 to 100 µm, for example, 10 to 80 µm such as 10 to 50 µm, preferably from 10 µm to 30 µm.

As schematically illustrated in FIGS. 2a-e, the medical dressings 40, 50, 60, 80, 90 may include an adhesive layer or coating 41, 42, 43 to adhere the medical dressing to a wound and/or the surrounding skin surface. In embodiments of the invention, this wound-facing adhesive layer or coating 41, 42, 43 may be a silicone based adhesive or an acrylic based adhesive, preferably the adhesive layer or coating is a silicone based adhesive. The term "coating" should, in accordance with the present invention, be understood as essentially one continuous layer on a surface, or a discontinuous cover on a surface.

The medical dressings 40, 50, 60, 80, 90 may furthermore comprise a release layer (not shown) that is releasably connected to the adhesive layer or coating 41, 42, 43 and can be removed prior to application. Suitable release layers comprise or consist of materials that have limited adhesion to the adhesive of the adhesive layer, if brought in contact with the same. Examples for such release layers are release papers that comprise a non-adhesive silicone or polyolefin layer.

Figure 2C:
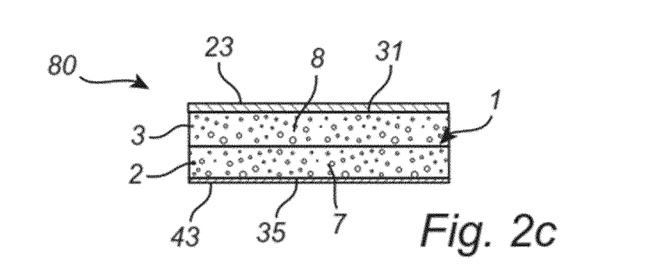
Figure 2D:
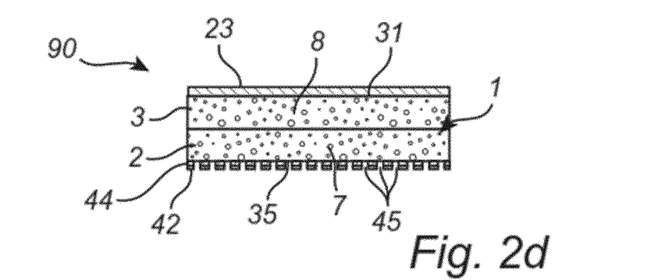

As shown in FIG. 2b and FIG. 2d, the medical dressings 50, 90 include a perforated layer 44, for example made of a polyurethane film, wherein an adhesive coating 42 is provided on the non-perforated portions of the perforated layer 44. The perforated layer 44 includes a plurality of openings 45 (or through holes) of any desirable size and shape.

The shape and size of the openings 45 may be adapted to achieve a desirable liquid transport from the wound to the above layers of the composite material 1.

In embodiments of the invention, as illustrated in FIG. 2b, the perforated layer 44 with the adhesive coating 42 may be provided on the wound facing surface 35 of the first foam layer 2, wherein the perforated layer 44 extends outside the peripheral portion of the foam layers 2,3 of the composite material 1 and is attached to the border portion 10 of the backing layer 21.

In alternative embodiments, as shown in FIG. 2d, the footprint of the perforated layer 44 corresponds to the footprint of the composite material 1. In embodiments of the invention, as shown in FIG. 2c, the adhesive coating 43 is provided directly on the wound facing surface 35 of the first foam layer 2. In embodiments of the invention, as shown in FIG. 2a, an adhesive coating 41 is provided on a continuous plastic film 46, for example a polyurethane film as discussed above, which continuous plastic film 46 is arranged adjacent to a peripheral portion of the layers of the composite material 1, wherein the continuous film 46 extends away from said peripheral portion and is attached to the border portion 10 of the backing layer 21. In further embodiments (not shown) and adhesive coating may be provided directly on a wound facing surface of the border portion 10 of the backing layer 21.

Figure 2E:
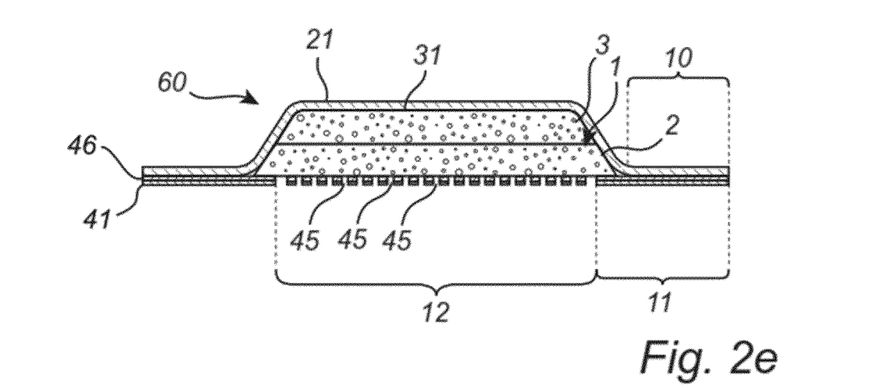

In embodiments of the invention, the medical dressing 60 as shown in FIG. 2e, includes a perforated layer 46 that comprises a central portion 12 underlying the composite material 1 and a border portion 11 extending outside the peripheral portion of the composite material 1, wherein the perforations 45 are only present in the central portion 12, such that fluid can be transferred through the perforations 45 and into the composite material 1, and wherein the perforated layer 46 is coated with an adhesive coating 41 as described above. The adhesive coating on the (non-perforated) border portion 11 of the perforated layer 46, provides a medical dressing 60 which has higher adhesive capabilities (due to larger adhesive contact area) vis-à-vis the medical dressing 50 shown in FIG. 2b (wherein perforations are present also in the border portion).

Figure 3:
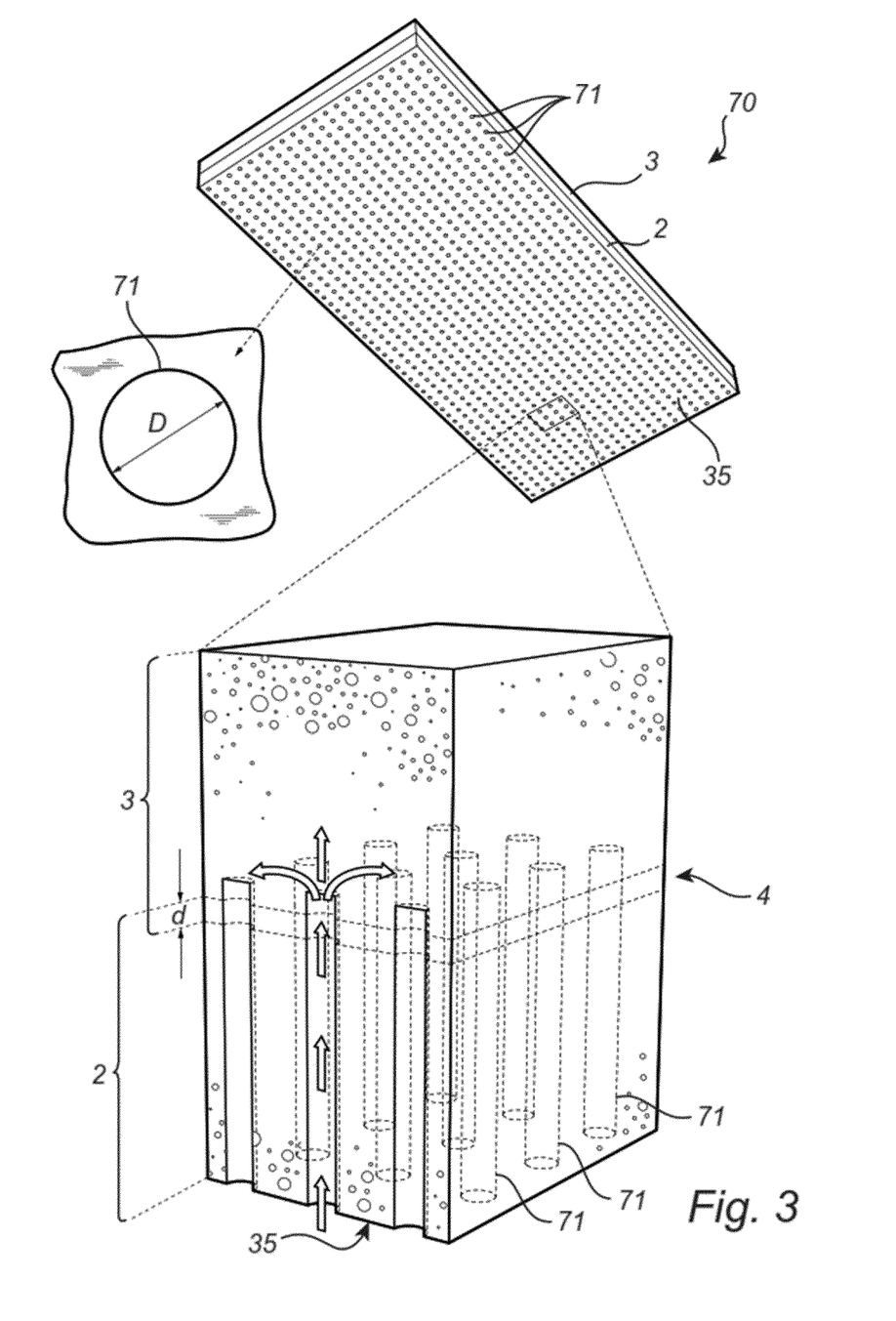
FIG. 3 is a schematic depiction of an embodiment of a composite material according to the second aspect of the invention.

FIG. 3 is a perspective view of an exemplary embodiment of a composite material 70, in particular in accordance with the second aspect of the present invention, wherein the composite material 70 comprises a first foam layer 2 comprising a first hydrophilic polyurethane foam material 7. The first foam layer 2 has a first side 35 adapted to face an area of application in use, preferably adapted to face a wound area. The composite material further comprises a second foam layer 3 comprising a second hydrophilic polyurethane foam material 8. The second foam layer 3 is bonded to a second side of the first foam layer 2, wherein the second side is opposite to the first side 35, and wherein an interfacial bonding volume 4 exists between the first foam layer 2 and the second foam layer 3. A plurality of channels 71 extends from the first side 35 of the first foam layer 2 through the entirety thereof and into at least a part of the second foam layer 3.

The channels 71 may typically have an average diameter (D) of from 0.1 mm to 4.0 mm, preferably from 0.5 mm to 3.0 mm, further preferably from 1.5 mm to 2.5 mm As schematically illustrated in FIG. 3, the plurality of channels 71 facilitates fluid transport from the first side 35 of the first foam layer 2, through the thickness of the first foam layer 2, and across the interface volume 4 between the first foam layer 2 and the second foam layer 3 and into the core of the second foam layer 3. As shown in FIG. 3, the plurality of channels 71 extends in vertical direction (i.e. z-direction or direction of thickness perpendicular to the plane of the layer 2).

The inventor has realized that fluid transport into and further through the first foam layer 2 and subsequently into the second foam layer 3 can be improved by providing a plurality of channels 71 that extends through the first foam layer 2, across the interfacial volume 4, and into an adjacent second foam layer 3. Thereby, the full absorption capacity of the composite material may be further optimized.

In particular, the fluid transport across an interface, e.g. the interfacial volume 4, between the first foam layer 2 and the second foam layer 3 can be improved by the plurality of channels 71 which extends through at least part of the second foam layer 3 and therefore also through the interface between the foam layers 2, 3.

In embodiments of the invention, the plurality of channels 71 extends at least a distance into the second foam layer 3, which distance corresponds to at least 5%, preferably at least 15%, further preferably at least 25% of the total thickness of the second foam layer.

The invention is further illustrated in the following Examples.

EXAMPLES

Method of Preparing a First Foam Layer

A first foam layer (for subsequent use in preparation of composite material) was prepared using the following steps (1-3): 1) An aqueous mixture was prepared (see table 1 for chemicals and concentrations); 2) the aqueous mixture was mixed with the selected prepolymer (see Table 1) at the specified ratio by weight (see Table 1) to give an emulsion mixture; 3) the emulsion mixture was poured onto and spread out on a casting paper (20×30 cm) and allowed to cure at standard condition (at room temperature) to give a foam thickness of about 3 mm (foam thickness is controlled by adapting the thickness of spread of the emulsion mixture in step 3). Chemicals used are commercially available as exemplified in the following: Baymedix® FP-505, HDI based prepolymer composition commercially available from Covestro; Trepol® B1, a TDI based prepolymer commercially available from Rynel Inc.; Polycat 77, commercially available from Air Products and Chemicals Inc.; Pluronic® L62, sodium bicarbonate and citric acid, are all commercially available from Sigma-Aldrich, Fisher Scientific, and/or BASF.

TABLE 1

| Single Foam Layer | Aqueous mixture | Prepolymer | Ratio: Aqueous mix./ Prepolymer (w/w) |
|---|---|---|---|
| Foam A (HDI) | sodium bicarbonate 1.5% w/w, Pluronic ® L62 0.01% w/w, and citric acid 0.002% w/w | Baymedix ® FP-505 | 0.2/1 |
| Foam B (TDI) | Pluronic ® L62 0.05% w/w | Trepol ® B-1 | 1.6/1 |
| Foam C (MDI) | Pluronic ® L62 0.4% w/w, Polycat 77 0.1% w/w | MDI prepolymer | 1.1/1 |

Method of Preparing a Composite Material

Composite materials according to embodiments of the invention were prepared, at standard laboratory conditions (at room temperature unless otherwise stated), by the following sequential steps (1-6): 1) an aqueous mixture was prepared (see table 2); 2) the aqueous mixture was mixed with the selected prepolymer (see table 2) at the specified ratio by weight (see Table 2) to give an emulsion mixture; 3) the emulsion mixture was poured onto and spread out on a casting paper (20×30 cm); 4) a single foam layer (one of Foam A, Foam B, or Foam C) (20×30 cm) was applied on top of the emulsion; 5) the emulsion mixture was allowed to cure at standard condition (at room temperature) to give a foam thickness of about 3 mm (foam thickness is controlled by adapting the thickness of spread of the emulsion mixture in step 3); and 6) the resulting composite product was dried in an oven at 40° C. for 10 minutes per side.

Steps 1 to 4 were performed in immediate sequential steps, wherein steps 1-4 should preferably be completed within less than 4 minutes to thereby ensure a desirable degree of curing (typically 50-90%, preferably 70-80%) in the emulsion mixture when step 4 is initiated. Test pieces were prepared by die-cutting the dried composite product to a size of approximately 10×10 cm.

TABLE 2

| Composite | Prepolymer | Aqueous mixture | Aqueous mix./ Prepolymer Ratio (w/w) | Single Foam Layer |
|---|---|---|---|---|
| Composite A (TDI-HDI) | Trepol ® B1 | Pluronic ® L62 0.15% w/w | 0.3/1 | Foam A |
| Composite B (HDI-TDI) | Baymedix ® FP 505 | sodium bicarbonate 1.5% w/w, Pluronic ® L62 0.01% w/w, and citric acid 0.002% w/w | 0.2/1 | Foam B |
| Composite C (TDI-MDI) | Trepol ® B1 | Pluronic ® L62 0.15% w/w | 0.3/1 | Foam C |

Unless indicated otherwise, all indications regarding percentages are meant to refer to percentage by weight. The degree of curing was measured by Fourier Transform Infrared Spectroscopy (FTIR). Viscosity was determined at 23° C. and in accordance with DIN 53019.

Method and Result of Measuring Thickness of Interfacial Bonding Volume

The thickness, or penetration depth, of the interfacial bonding volume was measured using a stereoscopic microscope with micrometer scale, that is, the interfacial bonding volume between the two foam layers was identified using the microscope and the thickness, corresponding to the depth of the interfacial bonding volume in the direction of the thickness of the layers/composite material, was measured using the micrometer scale. The thickness of the interfacial bonding volume in Composite A, B, and C, as measured accordingly, were all determined to be in the range of 20 to 50 µm.

Due to the comparatively low water content in the emulsion, as the polyurethane foam cures, essentially all or most of the water is contained within the cell walls as solvent/plasticizer and is therefore not free to migrate into the pre-made foam layer upon bonding the two foam layers together. Therefore, the thickness of the interfacial bonding volume between the two foams is comparatively small (in particular less than 200 µm).

Determination of Free Swell Absorptive (Fluid Absorption) Capacity

The free swell absorptive (or maximum absorption) capacity was determined according to EN 13726-1:2002 with the following small modifications: a test piece with the size 10×10 cm (thickness ca. 3 mm) was used and the free swell absorptive capacity per volume unit of test piece was calculated, i.e. mass (kg) of retained Solution A per volume ($m^3$). Weight per volume provides a more relevant measure (as compared with e.g. weight by weight as suggested in EN 13726-1:2002) when comparing hydrophilic foams with different densities. The weight per volume values can readily be converted to weight per weight by dividing the weight per volume value with the respective density value of the sample. The free swell absorptive capacity values of the foam layers A, B, and C, are presented in Table 3 below.

Determination of Fluid Retention Capacity

In accordance with the invention fluid retention capacity is determined by first measuring the free swell absorptive (or maximum absorption) capacity according to EN 13726-1: 2002. A rigid template, approximately the same size as the sample (10×10 cm) with a mass equivalent to 40 mmHg, is subsequently applied to sample (now being soaked Solution A according to EN 13726-1:2002). After 2 minutes the rigid template is removed and the sample weight is again measured and amount of residual moisture (retained Solution A) is calculated. The fluid retention capacity is calculated by dividing the amount of retained Solution A (kg) with the volume (m$^3$) of the sample. The retention value of the foam layers A, B, and C, are presented in Table 3 below.

TABLE 3

| Foam | Abs kg/m$^3$ | Ret kg/m$^3$ | % Ret |
|---|---|---|---|
| Foam A | 2185 | 1855 | 84.9 |
| Foam B | 1002 | 705 | 70.5 |
| Foam C | 1033 | 968 | 93.7 |

As can be seen in Table 3, both Foam A and Foam C have higher fluid retention capacity than Foam B, wherein e.g. Foam A has 263% greater retention capacity as compared with Foam B, and can thus suitably function as fluid retention layer in a composite material, wherein Foam B can suitably function as a wound fluid acquisition layer, in particular as Foam B has a greater speed of absorption than Foam A and Foam C.

In embodiments of the invention, the first foam layer may be embodied by foam layer B, and wherein the second foam layer may be embodied by foam layer A or foam layer C.

Determination of Speed of Absorption

In accordance with the invention, speed of absorption is determined according to TAPPI standard T558 OM-97 (which method inter alia evaluates the absorptive properties of a surface, as the remaining liquid volume on top of the specimen surface is measured as a function of time), wherein the test solution used herein is the Solution A from EN 13726-1, and droplet volume is 30 µl. The speed of absorption of the Foam B in the Composite material A, B, and C (i.e. the test solution was added to the Foam B of each of the Composite A, B, and C), was measured to be about 30 µl/sec. The speed of absorption of Foam A and Foam C was about 3 µl/sec and about 10 µl/sec, respectively.

The invention claimed is:

1. A composite material comprising:
a first foam layer comprising a first hydrophilic polyurethane foam material, wherein said first foam layer has a first side adapted to face an area of application in use,
a second foam layer comprising a second hydrophilic polyurethane foam material, wherein the fluid retention capacity of said second foam layer is at least 20% greater than the fluid retention capacity of said first foam layer, wherein said fluid retention capacity is defined as the capability of retaining Solution A having first absorbed a maximum amount of Solution A, according to EN 13726-1:2002, when exposed to a pressure of 40 mmHg for two minutes,
and wherein a plurality of channels extends from said first side of said first foam layer through the entire first foam layer into at least a portion of said second foam layer, wherein the channels have an average diameter of from 0.1 mm to 4.0 mm, wherein each channel of the plurality of channels is an open structure.

2. A composite material comprising:
a first foam layer comprising a first hydrophilic polyurethane foam material, wherein said first foam layer has a first side adapted to face an area of application in use,
a second foam layer comprising a second hydrophilic polyurethane foam material,
wherein an interfacial bonding volume exists between said first and said second foam layer,
wherein said interfacial bonding volume comprises a mixture of the materials making up said first and said second foam layer,
and wherein said interfacial bonding volume has a thickness of less than 200 µm,
and wherein a plurality of channels extends from said first side of said first foam layer through the entire first foam layer into at least a portion of said second foam layer, wherein the channels have an average diameter of from 0.1 mm to 4.0 mm, wherein each channel of the plurality of channels is an open structure.

3. A composite material comprising:
a first foam layer comprising a first hydrophilic polyurethane foam material, wherein said first foam layer has a first side adapted to face an area of application in use,
a second foam layer comprising a second hydrophilic polyurethane foam material,
wherein a plurality of channels extends from said first side of said first foam layer through the entire first foam layer into at least a portion of said second foam layer, wherein the channels have an average diameter of from 0.1 mm to 4.0 mm, wherein each channel of the plurality of channels is an open structure.

4. The composite material according to claim 3, wherein a fluid retention capacity of said second foam layer is at least 20% greater than a fluid retention capacity of said first foam layer, said fluid retention capacity is defined as the capability of retaining Solution A having first absorbed a maximum amount of Solution A, according to EN 13726-1:2002, when exposed to a pressure of 40 mmHg for two minutes.

5. The composite material according to claim 2, wherein at least one physical property of the material comprised in the interfacial bonding volume is different vis-à-vis the material making up said first foam layer and said second foam layer, respectively.

6. The composite material according to claim 3, wherein the thickness of the first foam layer is less than the thickness of the second foam layer.

7. The composite material according to claim 3, wherein said second foam layer has a fluid retention capacity of at least 800 kg/m3.

8. The composite material according to claim 3, wherein said first foam layer has a speed of absorption of at least 10 µL/sec, as measured according to TAPPI standard T558 OM-97, using 30 µL Solution A, according to EN 13726-1:2002, as test solution.

9. The composite material according to claim 3, wherein at least one of said first foam layer and/or said second foam layer is obtained by a process, in which an aqueous mixture comprising a prepolymer, leading to the hydrophilic polyurethane foam layer, comprises less than 40% of water.

10. The composite material according to claim 3, wherein said first hydrophilic polyurethane foam material is obtained from a first prepolymer comprising or being an isocyanate-capped polyol or isocyanate-capped polyurethane, and/or wherein said second hydrophilic polyurethane foam material is obtained from a second prepolymer comprising or being an isocyanate-capped polyol or isocyanate-capped polyurethane.

11. The composite material according to claim 10, wherein said polyol is selected from the group consisting of a polyester polyol, polyacrylate polyol, polyurethane polyol, polycarbonate polyol, polyether polyol, polyesterpolyacrylate polyol, polyurethane polyacrylate polyol, polyurethane polyester polyol, polyurethane polyether polyol, polyurethane polycarbonate polyol, and polyester polycarbonate polyol.

12. The composite material according to claim 10, wherein said first and/or second prepolymer derive(s) from a reaction between a polyol, and a diisocyanate compound selected from the group consisting of hexamethylene diisocyanate (HDI), toluene diisocyanate (TDI), methylene diphenyl diisocyanate (MDI), and isophorone diisocyanate (IPDI), or any mixture thereof.

13. A medical dressing comprising a composite material according to claim 3.

14. The medical dressing according to claim 13, wherein said medical dressing further comprises at least one further layer.

15. A method for producing the composite material of claim 3, comprising the steps of:
   (i) preparing an aqueous mixture comprising a polyurethane prepolymer, wherein the water content of said aqueous mixture is less than 40% w/w relative to the total weight of said aqueous mixture;
   (ii) applying said aqueous mixture from step (i) onto a carrier material;
   (iii) applying, before said aqueous mixture is essentially completely cured, an already cured hydrophilic polyurethane foam layer on top of said aqueous mixture as cast onto said carrier material in step (ii);
   (iv) allowing said aqueous mixture to essentially completely cure, thereby producing a composite material comprising a first foam layer comprising a first hydrophilic polyurethane foam material and a second foam layer comprising a second hydrophilic polyurethane foam material; and
   (v) forming the plurality of channels extending from said first side of said first foam layer through the entire first foam layer into at least a portion of said second foam layer, wherein the channels have an average diameter of from 0.1 mm to 4.0 mm, wherein each channel of the plurality of channels is an open structure.

16. The method according to claim 15, wherein the degree of curing of said aqueous mixture is between 50 to 90%, at the stage of applying said layer of an already cured hydrophilic polyurethane foam layer in step (iii).

* * * * *